US009282905B2

(12) United States Patent
Wang

(10) Patent No.: US 9,282,905 B2
(45) Date of Patent: Mar. 15, 2016

(54) METHODS FOR LASER SPECKLE CONTRAST IMAGING OF BLOOD PERFUSION

(71) Applicant: University of Washington through its Center for Commercialization, Seattle, WA (US)

(72) Inventor: Ruikang K. Wang, Bellevue, WA (US)

(73) Assignee: University of Washington Through its Center for Commercialization, Seattle, WA (US)

(*) Notice: Subject to any disclaimer, the term of this patent is extended or adjusted under 35 U.S.C. 154(b) by 128 days.

(21) Appl. No.: 14/289,999

(22) Filed: May 29, 2014

(65) Prior Publication Data

US 2014/0357990 A1 Dec. 4, 2014

Related U.S. Application Data

(60) Provisional application No. 61/828,459, filed on May 29, 2013.

(51) Int. Cl.
*A61B 5/05* (2006.01)
*A61B 5/026* (2006.01)
*A61B 5/00* (2006.01)
*G02B 27/48* (2006.01)

(52) U.S. Cl.
CPC ............. *A61B 5/0261* (2013.01); *A61B 5/7246* (2013.01); *A61B 5/445* (2013.01); *A61B 5/7257* (2013.01); *G02B 27/48* (2013.01)

(58) Field of Classification Search
CPC .... A61B 5/0261; A61B 5/7246; A61B 5/445; A61B 5/7257; G02B 27/48
See application file for complete search history.

(56) References Cited

U.S. PATENT DOCUMENTS

| 7,113,817 | B1 | 9/2006 | Winchester, Jr. |
|---|---|---|---|
| 7,817,256 | B2 | 10/2010 | Fujii |
| 8,285,003 | B2 | 10/2012 | Fujii |
| 2012/0095354 | A1 | 4/2012 | Dunn |

OTHER PUBLICATIONS

Boas and A. K. Dunn, "Laser speckle contrast imaging in biomedical optics," J. Biomed. Opt. 15(1), 011109 (2010).
Bonner and P. Nossal, "Model for laser Doppler measurements of blood flow in tissue," Appl. Opt. 20(12), 2097-2107 (1981).
Briers, G. Richards, and X. W. He, "Capillary blood flow monitoring using laser speckle contrast analysis (LASCA)," J. Biomed. Opt. 4(1), 164-175(1999).

(Continued)

*Primary Examiner* — Mark Remaly
(74) *Attorney, Agent, or Firm* — McDonnell Boehnen Hulbert & Berghoff LLP

(57) ABSTRACT

A method for imaging blood flow through target tissue is disclosed. An example method may include (a) directing a light beam at a blood-perfused target tissue, (b) reflecting the directed light beam off of static target tissue and flowing cells, (c) capturing a plurality of digital images of interference patterns of the reflected light in a plurality of successive frames, (d) measuring a light intensity of at least one pixel of each digital image, where the at least one pixel corresponds to an identical pair of coordinates in each successive frame, (e) comparing the measured light intensity of the at least one pixel of each digital image to the measured light intensity of the at least one pixel of an adjacent frame at the identical pair of coordinates and (f) determining a compiled light intensity for the at least one pixel for an aggregate motion contrast.

19 Claims, 8 Drawing Sheets

(56) References Cited

OTHER PUBLICATIONS

Briers, S. Webster, "Quasi real-time digital version of single-exposure speckle photography for full-field monitoring of velocity or flow fields," Opt. Commun. 116(1- 3), 36-42(1995).

Cheng, Q. Luo, S. Zeng, S. Chen, J. Cen, H. Gong, "Modified laser speckle imaging method with improved spatial resolution," J. Biomed. Opt. 8(3), 559-564 (2003).

Dunn, A. Devor, H. Bolay, M. L. Andermann, M. A. Moskowitz, A. M. Dale, and D. A. Boas, "Simultaneous imaging of total cerebral hemoglobin concentration, oxygenation, and blood flow during functinoal activation," Opt. Lett. 28(1), 28-30(2003).

Forrester, C. Stewart, J. Tulip, C. Leonard, R. C. Bray, "Comparison of laser speckle and laser Doppler perfusion imaging: measurement in human skin and rabbit articular tissue," Med. Biol. Eng. Comput. 40(6), 687-697(2002).

Kalchenko, A. Brill, M. Bayewitch, I. Fine, V. Zharov, F. Galanzha, V. Tuchin, and A. Harmelin, "In vivo dynamic light scattering imaging of blood coagulation," J. Biomed. Opt. 12(5), 052002(2007).

Kirkpatrick, D. D. Duncan, and E. M. Wells-Gray, "Detrimental effects of speckle-pixel size matching in laser speckle contrast imaging," Opt. Lett. 33(24), 2886-2888(2008).

Li, S. Ni, L. Zhang, S. Zeng, and Q. Luo, "Imaging cerebral blood flow through the intact rat skull with temporal laser speckle imaging," Opt. Lett. 31(12), 1824- 1826(2006).

Murari, K. et al., Contrast-Enhanced Imaging of Cerebral Vasculature with Laser Speckle, 46 Applied Optics 5340-46 (Aug. 2007).

Parthasarathy, E. L. Weber, L. M. Richards, D. J. Fox, and A. K. Dunn, "Laser speckle contrast imaging of cerebral blood flow in humans during neurosurgery: a pilot clinical study," J. Biomed. Opt. 15(6), 066030(2010).

Parthasarathy, W. J. Tom, A. Gopal, X. Zhang, and A. K. Dunn, "Robust flow measurement with multi-exposure speckle imaging," Opt. Express. 16(3), 1975-1989(2008).

Qin, L. Shi, S. Dziennis, R. Reif, and R. K. Wang, "Fast synchronized dualwavelength laser speckle imaging system for monitoring hemodynamic changes in a stroke mouse model," Opt. Lett. 37(19), 4005-4007(2012).

Yuan, A. Devor, D. A. Boas, and A. K. Dunn, "Determination of optimal exposure time for imaging of blood flow changes with laser speckle contrast imaging," Appl. Opt. 44(10), 1823-1830(2005).

Zakharov, P. et al., Dynamic Laser Speckle Imaging of Cerebral Blood Flow, 17 Optics Express 13904-17 (Aug. 2009).

Briers. J.D., et al., "Capillary Blood Flow Monitoring Using Laser Speckle Contrast Analysis (LASCA)," Journal of Biomedical Optics, 4(1), p. 164-175 (Jan. 1999).

Murari, K., et al., "Contrast-enhanced imaging of cerebral vasculature with laser speckle," Applied Optics, vol. 46, No. 22, p. 5340-5346 (Aug. 1, 2007).

Yuan, Shuai, et al., "Determination of optimal exposure time for imaging of blood flow changes with laser speckle contrast imaging," Optical Society of America, vol. 44, No. 10, p. 1823-1830 (Apr. 1, 2005).

Zakharov, P., et al. "Dynamic laser speckle imaging of cerebral blood flow," Optics Express, vol. 17, No. 16, p. 13904-13917 (Aug. 3, 2009).

METHODS FOR LASER SPECKLE CONTRAST IMAGING OF BLOOD PERFUSION

CROSS-REFERENCE TO RELATED APPLICATION

This application claims the benefit of the filing date of U.S. Provisional Patent Application Ser. No. 61/828,459, filed May 29, 2013, which is hereby incorporated by reference in its entirety.

BACKGROUND

Unless otherwise indicated herein, the materials described in this section are not prior art to the claims in this application and are not admitted to be prior art by inclusion in this section.

Laser speckle contrast imaging ("LSCI") is a wide-field 2D imaging technique capable of rapid mapping dynamic blood flow within tissue beds in vivo. In LSCI, a digital camera may be used to record speckle patterns (i.e., coherent interference) formed by the coherent addition of scattered laser light propagating within tissue. The statistical properties of speckle pattern are dependent on the coherence of the incident light and the tissue optical properties. For a perfused tissue, the motion of red blood cells ("RBCs"), for example, may cause localized intensity fluctuations in the speckle pattern that may be analyzed with spatial, temporal, or combined spatiotemporal contrast algorithms to provide a dynamic blood perfusion map, indicating blood supply to the living tissue of interest.

LSCI is typically used for pre-clinical and clinical applications in the monitoring of, cerebral blood flow, and skin tissue perfusion during the wound healing, for example. LSCI is, however, traditionally married with a difficulty in visualizing small blood vessels. This poor visualization occurs even when the exposure time of the detector is long, because the technique may fail to account for scattering from static tissue elements.

An alternative visualization method is optical coherence tomography ("OCT") that is a non-invasive method for providing high resolution (~10 μm) and three-dimensional images of microstructures within biological tissues. Optical microangiography ("OMAG") is a technique for processing an OCT dataset that allows extraction of three-dimensional microvasculature from the OCT images, with capillary resolution. OMAG has been used in a variety of applications which include tracking wounds and burns in mouse ear, imaging of the human corneo-scleral limbus and human retina, studies of mouse brain and others, but often suffers from background noise that arises from the stationary tissue background that may obscure the visualization and quantification of the capillary blood flows within tissue beds.

SUMMARY

Example embodiments provide motion contrast of dynamic speckle patterns to noninvasively visualize the distribution of blood flow within microcirculatory tissue beds in vivo, including capillaries. The methods for motion contrast imaging may significantly suppress the effect of static scattering on the final imaging result, leading to enhanced visibility and quantification of the functional blood vessels, including capillaries. This has the benefit of providing images that better indicate healing in a wound or blood flow through tissues or organs for purposes of diagnosis or monitoring of treatment, for example.

Thus, in one aspect, a method for imaging blood flow through target tissue is provided including the steps of (a) directing a light beam at a blood-perfused target tissue, (b) reflecting the directed light beam off of static target tissue and flowing cells, (c) capturing a plurality of digital images of interference patterns of the reflected light in a plurality of successive frames, (d) measuring, via a processor, a light intensity of at least one pixel of each digital image, wherein the at least one pixel corresponds to an identical pair of coordinates in each successive frame, (e) comparing the measured light intensity of the at least one pixel of each digital image to the measured light intensity of the at least one pixel of an adjacent frame at the identical pair of coordinates thereby enhancing a light saturation profile for the at least one pixel of each frame and (f) determining, via the processor, a compiled light intensity for the at least one pixel for an aggregate motion contrast image based upon the enhanced light saturation profile of the at least one pixel for each frame.

In a second aspect, a method for imaging blood flow through target tissue is provided including the steps of (a) directing a light beam at a blood-perfused target tissue, (b) reflecting the directed light beam off of static target tissue and flowing cells, (c) capturing a plurality of digital images of interference patterns of the reflected light in a plurality of successive frames (N), (d) measuring, via a processor, a light intensity of at least one pixel of each digital image, wherein the at least one pixel corresponds to an identical pair of coordinates (x, y) in each successive frame, wherein $I_i(x,y)$ is the light intensity of the at least one pixel (x, y) in a frame i, wherein the frame i corresponds to i=1, 2, ... N, (e) comparing the measured light intensity of the at least one pixel (x, y) of each digital image to the measured light intensity of the at least one pixel (x, y) of an adjacent frame at the identical pair of coordinates (x, y) thereby enhancing a light saturation profile for the at least one pixel of each frame and (f) determining, via the processor, a compiled light intensity for the at least one pixel (x, y) for an aggregate motion contrast image based upon the enhanced light saturation profile of the at least one pixel (x, y) for each frame.

These as well as other aspects, advantages, and alternatives, will become apparent to those of ordinary skill in the art by reading the following detailed description, with reference where appropriate to the accompanying drawings.

DETAILED DESCRIPTION

Figure 1:
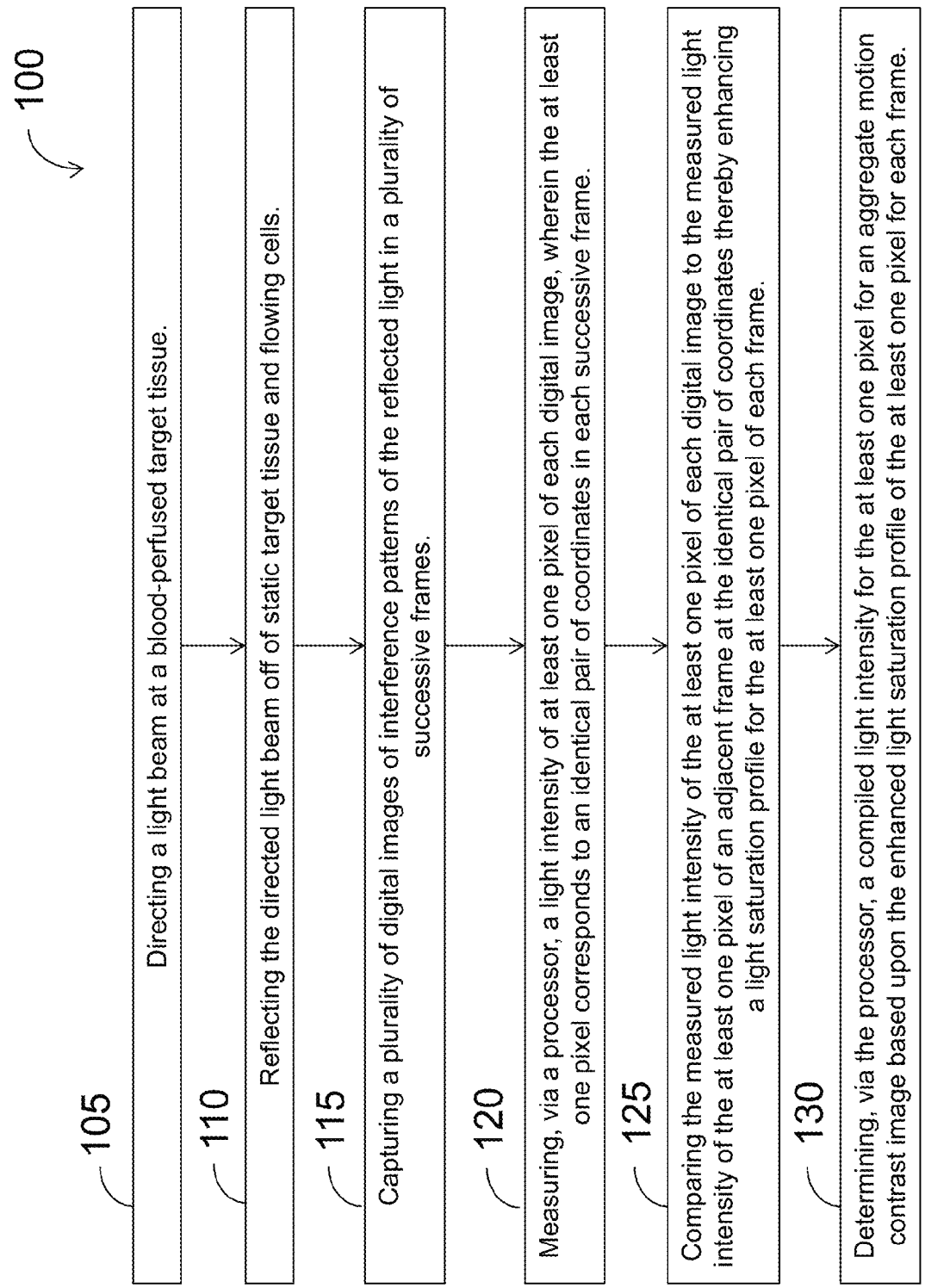
FIG. 1 is a flow chart of a method of noninvasive visualization of the distribution of blood flow within a tissue bed, according to one example embodiment.

Example methods of noninvasive visualization of the distribution of blood flow within a tissue bed are described herein. Any example embodiment or feature described herein is not necessarily to be construed as preferred or advantageous over other embodiments or features. The example embodiments described herein are not meant to be limiting. It will be readily understood that certain aspects of the disclosed methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

As used herein, "about" means +/−5%.

As used herein, "light beam" means light capable of producing optical interference patterns due to its coherence property, such as a laser beam or a broadband white light.

As used herein, "flowing cells" include cells capable of reflecting the light beam that are moving or capable of moving through various systems in living tissues. Flowing cells may include red blood cells, white blood cells, lymph, or exogenous particles, among other possibilities.

As used herein, "an aggregate motion contrast image" means a digital image compiled based upon pixel-specific data derived from a plurality of digital images of the same target tissue taken in time-successive frames.

As used herein, a "light saturation profile" means a refined light intensity associated with a pixel of a digital image that better reflects the true nature of the target tissue (i.e., static tissue or flowing cells) captured by a given pixel.

The method may be used to monitor blood flow within a living tissue, for example a brain, eye, skin, heart, liver, pancreas, esophagus, stomach or colon, among other possibilities. The tissue may include a wound bed or healthy tissue. The method may be employed to monitor wound healing or progression, or to diagnose or monitor treatment of a condition or disease of a target tissue. In one embodiment, the method may be employed to monitor therapeutic efficacy of a treatment or intervention of disease conditions that have vascular involvement. The disease condition may include, but is not limited to, a skin wound and its treatment, cancer and its treatment, tissue inflammation and its treatment, eye diseases and their treatments, e.g. diabetic retinopathy, age-related macular degeneration, glaucoma, macular telangiectasia, etc.

In dermatology, for example, the superficial dermal plexus alone may be particularly affected by the presence of disease (e.g. psoriasis, eczema, scleroderma), malformation (e.g. port-wine stain, hemangioma, telangiectasia), or trauma (e.g. irritation, wound, burn) or cancer. In these situations, the present methods may be utilized to beneficially monitor the localized blood flow that innervates the tissue—and to do so at user-specified discrete spatial locations in either the superficial or deep dermis, without physically disturbing the target tissue. In some embodiments, the methods may also be used to accurately visualize micro-vascular networks and to quantify tissue perfusion under normal and pathophysiologic conditions to evaluate existing and emerging therapeutic strategies in the treatment of neurovascular diseases, for example ischemic and hemorrhagic stroke, vascular dementia, traumatic brain injury, inflammation, and some seizure disorders, and in developing potential drugs to support or limit neovascular growth, such as in treatment of cancer and neovascular age related macular degeneration. There may be disease-specific parameters and quantifiable metrics or observations to indicate presence of a disease and/or to permit monitoring of a disease (e.g., healing or worsening of a condition). These disease-specific parameters (such as vascular density and rate of blood flow) may also vary based on patient-specific variables such as age and/or gender, for example.

Figure 2:
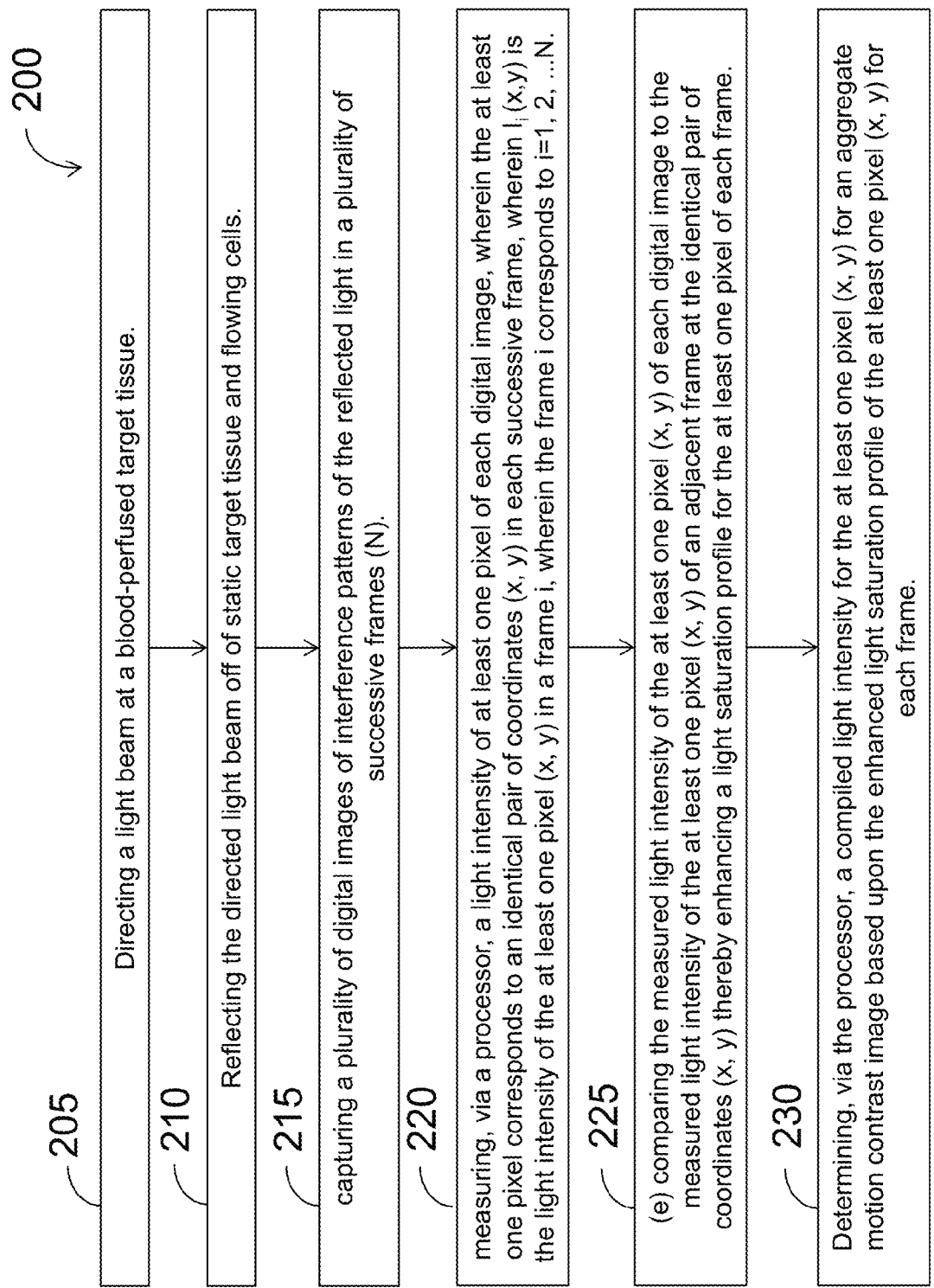
FIG. 2 is a flow chart of a method of noninvasive visualization of the distribution of blood flow within a tissue bed, according to one example embodiment.

FIG. 1 is a flow chart of a method 100 for imaging blood flow through target tissue, according to one example embodiment. Example methods, such as method 100 of FIG. 1 and method 200 of FIG. 2, may be carried out by an operator or a control system. A control system may take the form of program instructions stored on a non-transitory computer readable medium and a processor that executes the instructions. However, a control system may take other forms including software, hardware, and/or firmware.

As shown by block 105, method 100 involves directing a light beam at a blood-perfused target tissue. Then, at block 110, the directed light beam is reflected off of static target tissue and flowing cells. Note that the light beam does not reflect off of the plasma in the vascular system or the lymph in the lymphatic system. Next, at block 115 a plurality of digital images are captured of interference patterns of the reflected light in a plurality of successive frames. In one embodiment, each of the plurality of digital images may be a laser-speckle image produced by scattering of the light beam off of the target tissue and flowing cells. In another embodiment, each of the plurality of digital images may be an optical coherence tomography cross-section image produced by an optical coherence tomography imaging system when the light beam is scattered off of the target tissue and flowing cells.

In addition, in one embodiment, the plurality of successive frames may be captured at a sampling frequency ranging from 1 Hz to 1,000,000 Hz. In a another embodiment, a camera exposure time per frame may range from about 1 microsecond to about 1 second. In one exemplary embodiment, the plurality of successive frames may be 25 successive frames and the camera exposure time per frame may be about 40 ms, for example.

At block 120, a light intensity of at least one pixel of each digital image is measured via a processor. The at least one pixel corresponds to an identical pair of coordinates in each successive frame. In one embodiment, the light intensity of a plurality of pixels is measured and processed. Then the measured light intensity of the at least one pixel of each digital image is compared to the measured light intensity of the at least one pixel of an adjacent frame at the identical pair of coordinates, at block 125, thereby enhancing a light saturation profile for the at least one pixel of each frame. In one embodiment, step 125 may include differentiating the value of the measured light intensity for the at least one pixel of each digital image by the value of the measured light intensity for the at least one pixel of the adjacent frame at the identical pair of coordinates thereby obtaining a light intensity difference for the at least one pixel of each frame. In another embodiment, step 125 may include dividing the value of the measured light intensity for the at least one pixel of each digital image by the value of the measured light intensity for the at least one pixel of the adjacent frame at the identical pair of coordinates thereby obtaining a light intensity quotient for the at least one pixel of each frame. In another embodiment, step 125 may further include determining the difference between the light intensity quotient for the at least one pixel of each digital image and a light intensity quotient for the at least one pixel of the adjacent frame at the identical pair of coordinates. Differentiating, dividing and determining the difference in light intensity quotients may each further refine the visual aspects of the aggregate motion contrast image to better highlight micro-vasculature like capillaries. In yet another embodiment, step 125 may further include taking the absolute operation of the values resulted from differentiating, dividing or determining the difference in light intensity quotients.

Subsequently, at block 130, a compiled light intensity for the at least one pixel for an aggregate motion contrast image is determined by the processor based upon the enhanced light saturation profile of the at least one pixel for each frame. In one embodiment, step 130 may include determining for each pixel of the motion contrast image a mean of the light intensity differences, a mean of the light intensity quotients or a mean of the differences in light intensity quotients. In another embodiment, step 130 may include determining for the at least one pixel of the aggregate motion contrast image a sample standard deviation of the light intensity differences, a sample standard deviation of the light intensity quotients for the at least one pixel of each frame or a sample standard deviation of the differences in light intensity quotients for the at least one pixel of each frame.

In an alternative embodiment, step 125 may include performing Fourier transformation of the light intensity differences for the at least one pixel of each frame, of the light intensity quotients for the at least one pixel of each frame or of the differences in light intensity quotients for the at least one pixel of each frame. And then transforming a signal associated with the at least one pixel of the aggregate motion contrast image. In this embodiment, step 130 may include performing high-pass filtering of a Fourier-transformed signal for the at least one pixel of the aggregate motion contrast image. The mean, standard deviation and/or Fourier transformation approaches may be used separately or together in various orders of operation to achieve further refinement of the aggregate motion contrast image.

In one embodiment, the method 100 may further include the step of a processor storing a data file containing the aggregate motion contrast image. In another embodiment, the method 100 may also include the step of a processor sending a message including a data file containing the aggregate motion contrast image. The data file may be stored on or the message may be sent to an email server, a hard drive, a flash-drive, a temporary storage drive, a cell phone, a computer or a handheld electronic device, among other possibilities.

In a further embodiment, the aggregate motion contrast image may be displayed on a display device, such as a monitor, a laptop, a computer screen, a television screen, a handheld electronic device or a cell phone, among other possibilities.

In a second aspect, a method 200 for imaging blood flow through target tissue is shown in the flow chart of FIG. 200. As shown at block 205, method 200 includes directing a light beam at a blood-perfused target tissue and then, at block 210, reflecting the directed light beam off of static target tissue and flowing cells. Next, at block 215, a plurality of digital images of interference patterns of the reflected light is captured in a plurality of successive frames (N). At block 220, a light intensity of at least one pixel of each digital image is measured via a processor. The at least one pixel corresponds to an identical pair of coordinates (x, y) in each successive frame, where $I_i(x,y)$ is the light intensity of the at least one pixel (x, y) in a frame i, and the frame i corresponds to i=1, 2, ... N.

Then, the measured light intensity of the at least one pixel (x, y) of each digital image is compared to the measured light intensity of the at least one pixel (x, y) of an adjacent frame at the identical pair of coordinates (x, y), at block 225, thereby enhancing a light saturation profile for the at least one pixel of each frame. In one embodiment, step 225 may include determining a light intensity difference for the at least one pixel of each frame based upon $D_i(x, y)=I_i(x, y)-I_{i+1}(x, y)$. In another embodiment, step 225 may include determining a light intensity quotient for the at least one pixel of each frame based upon $D_i(x, y)=I_i(x, y)/I_{i+1}(x, y)$. In another embodiment, step 225 may further include determining a difference in the light intensity quotients for the at least one pixel (x, y) of each frame based upon $\Delta D_i(x, y)=[D_i(x, y)-D_{i+1}(x, y)]/2$. In yet another embodiment, step 225 may further include taking an absolute operation of the differences, i.e., $D_i(x, y)=|I_i(x, y)-I_{i+1}(x, y)|$ or $\Delta D_i(x, y)=|D_i(x, y)-D_{i+1}(x, y)|/2$.

Subsequently, at block 230, a compiled light intensity for the at least one pixel (x, y) for an aggregate motion contrast image is determined by the processor, based upon the enhanced light saturation profile of the at least one pixel (x, y) for each frame. In one embodiment, step 230 may include determining for the at least one pixel (x, y) of the aggregate motion contrast image a mean of the light intensity quotients or a mean of the light intensity differences based upon $$\overline{D}(x, y) = \frac{1}{N}\sum_{i=1}^{N} D_i(x, y)$$

or a mean of the differences in the light intensity quotients based upon $$\overline{\Delta D}(x, y) = \frac{1}{N}\sum_{i=1}^{N} \Delta D_i(x, y).$$

In an alternative embodiment, step 230 may include determining for the at least one pixel of the aggregate motion contrast image a sample standard deviation of the light intensity quotients or a sample standard deviation of the light intensity differences of the at least one pixel (x, y) of each frame based upon:

$$\sigma_m(x, y) = \sqrt{\sum_{i=1}^{N}[D_i(x, y) - \overline{D}(x, y)]^2/(N-1)}$$

or a sample standard deviation of the difference in light intensity quotients of the at least one pixel (x, y) of each frame based upon:

$$\sigma_m(x, y) = \sqrt{\sum_{i=1}^{N} [\Delta D_i(x, y) - \overline{\Delta D}(x, y)]^2 / (N - 1)}.$$

In an alternative embodiment, the comparison of step 225 may include performing Fourier transformation of the light intensity quotients or of the light intensity differences, $D_i(x, y)$, for the at least one pixel of each frame or of the differences in light intensity quotients, $\Delta D_i(x, y)$, for the at least one pixel of each frame. And then transforming a signal associated with the at least one pixel of the aggregate motion contrast image. Then step 230 may include performing high-pass filtering of the Fourier-transformed signal for the at least one pixel of the aggregate motion contrast image.

The above detailed description describes various features and functions of the disclosed methods to enhance the visibility and quantification of the blood flows within tissue beds through processing the digital images captured by an optical imaging system/technology. The optical imaging technologies to produce such digital images may include, but are not limited to, laser speckle imaging, optical coherence tomography, confocal microscopy (including multiphoton microscopy), scanning laser ophthalmoscope, or adaptive optics scanning laser ophthalmoscope, among other possibilities.

The above detailed description describes various features and functions of the disclosed methods with reference to the accompanying figures. While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

EXAMPLE 1

Motion-Contrast Laser Speckle Imaging of Microcirculation Within Tissue Beds In Vivo This example describes a new motion enhanced LSCI ("mLSCI") method for noninvasive imaging of blood flows, including capillary flows. Specifically, upon a laser beam shining into a static tissue, speckle pattern remains constant over time. However, dynamic speckle results when there are scattering particles that are in motion, e.g., RBCs moving in patient blood vessels, leading to time-varying fluctuation in light intensity detected by a digital camera. Provided that the camera detector has sufficient temporal response to record the time-varying speckle due to moving RBCs, the spatial or temporal speckle contrast may be used to visualize dynamic blood flow. In the case of a temporal contrast method in which a series of N speckle patterns (frames) are recorded over a time period of T, the speckle contrast $K_t$ at pixel $(x, y)$ is calculated by:

$$K_t(x, y) = \frac{\sigma_t(x, y)}{\langle I(x, y) \rangle} \quad (1)$$

$$= \sqrt{\frac{1}{N-1} \left\{ \sum_{i=1}^{N} [I_i(x, y) - \langle I(x, y) \rangle]^2 \right\}} / \langle I(x, y) \rangle,$$

to contrast the blood flow, where $\sigma_t$ is the temporal standard deviation, $\langle I(x, y) \rangle$ is the mean intensity of pixel $(x, y)$ over N frames, $I_i(x, y)$ is the light intensity recorded by the camera at the $i^{th}$ laser speckle image ($i=1, 2, \ldots N$). While efficient, this method (including spatial contrast approach) may not provide optimal treatment to suppress the background scattering signals from the static tissue elements, leading to reduced visibility of small blood vessels, in particular the capillaries.

This example sets forth an alternative analysis method to contrast the blood flow from the static tissue. In this method, a division operation is performed on adjacent digital images, i.e., $D_i(x, y) = I_i(x, y)/I_{i+1}(x, y)$. Because the diffuse reflectance of background static tissue recorded by the digital camera remains relatively constant, this operation of division emphasizes the scattering particles in motion. Then the differences between two consecutive division images, $\Delta D_i(x, y) = [D_i(x, y) - D_{i+1}(x, y)]/2$ may be calculated to eliminate or suppress background signals due to static tissue elements and to highlight fine changes between adjacent frames. Finally, a standard deviation $\sigma_m(x, y)$ may be used to provide the blood flow contrast in the resulting mLSCI images, which is given by:

$$\sigma_m(x, y) = \sqrt{\sum_{i=1}^{N} [\Delta D_i(x, y) - \overline{\Delta D}(x, y)]^2 / (N - 1)}, \quad (2)$$

where $\overline{\Delta D}(x, y)$ is the mean of difference images, $$\overline{\Delta D}(x, y) = \frac{1}{N} \sum_{i=1}^{N} \Delta D_i(x, y).$$

Figure 3:
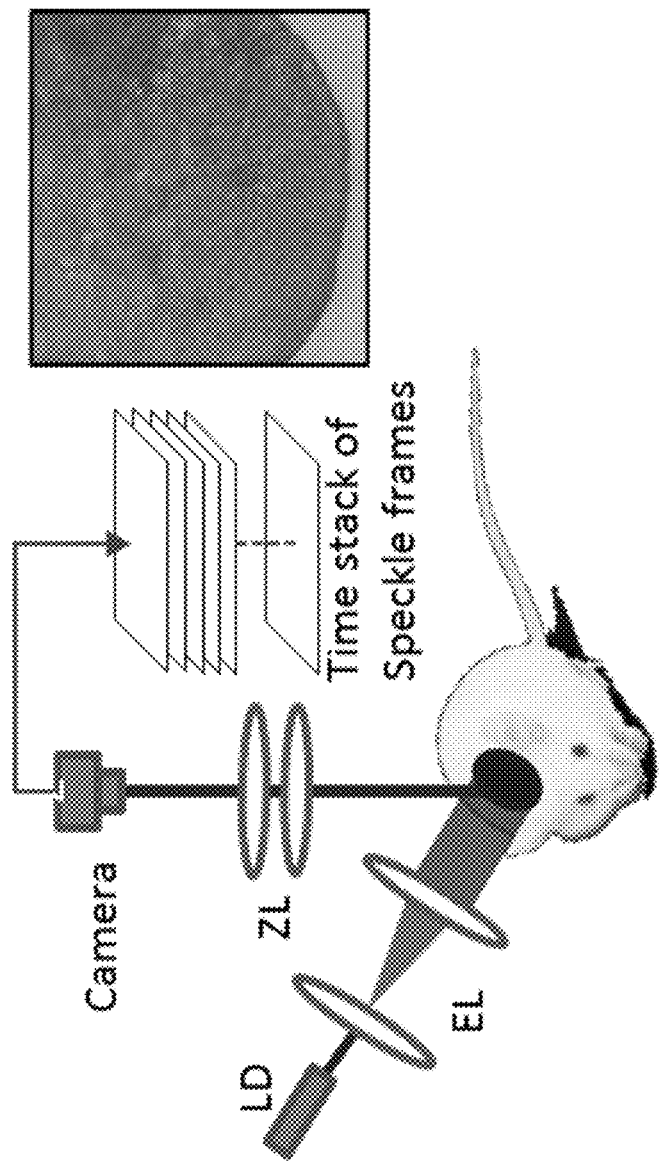
FIG. 3 shows a schematic of a motion enhanced LSCI imaging system, according to one embodiment, where LD is a 780 nm laser diode, EL is a beam expanding lens and ZL is a zoom lens. Also shown is a photograph of a mouse ear flap.

The schematic of the experimental setup is shown in FIG. 3, similar to a typical wide-field setup for laser speckle contrast imaging. A collimated beam from a diode laser with a wavelength of $\lambda=780$ nm is expanded and then uniformly illuminates the sample at an incident angle of ~60° from the tissue normal direction. The backscattered light from the sample is transmitted to a zoom lens (Zuiko, 75-150 mm, f/4.0, USA) and then received by a fast CMOS camera (Basler A504k, Germany). The camera is configured to acquire images with a size of 1000×1000 pixels. The magnification of the system is carefully adjusted to meet the requirement of sampling the speckles for faithful LSCI analysis, providing a field of view of ~6×6 mm². The system has a calibrated spatial resolution of ~15 μm, To demonstrate the enhanced capability of the proposed method to visualize the dynamic blood flow, particularly the functioning capillaries, blood perfusion was imaged within the ear flap of a mouse aged ~4 weeks. A photograph of the mouse ear is provided in the insert of FIG. 3 where the imaged area was near the ear edge. During experiments, the animal was anesthetized with 2% isoflurane (0.2 L/min $O_2$, 0.8 L/min air), and its external ear was gently attached to a plastic platform under the mLSCI system for imaging. The experiments did not involve any surgical procedures on the animal. The animal handling was in accordance with protocols approved by the University of Washington Institutional Animal Care and Use Committee.

To investigate how the camera exposure time has an effect on the final mLSCI results, laser speckle images of the mouse ear were captured with the camera set at 250 frames per second ("fps"), 100 fps and 25 fps, corresponding to the camera exposure times Δt of 4 ms, 10 ms and 40 ms, respectively. Temporal contrast (Eq.1) and motion enhanced contrast (Eq.2) in each case were then evaluated from 100 successive frames of diffuse speckle patterns recorded by the camera. The results are shown in FIG. 4.

Figure 4:
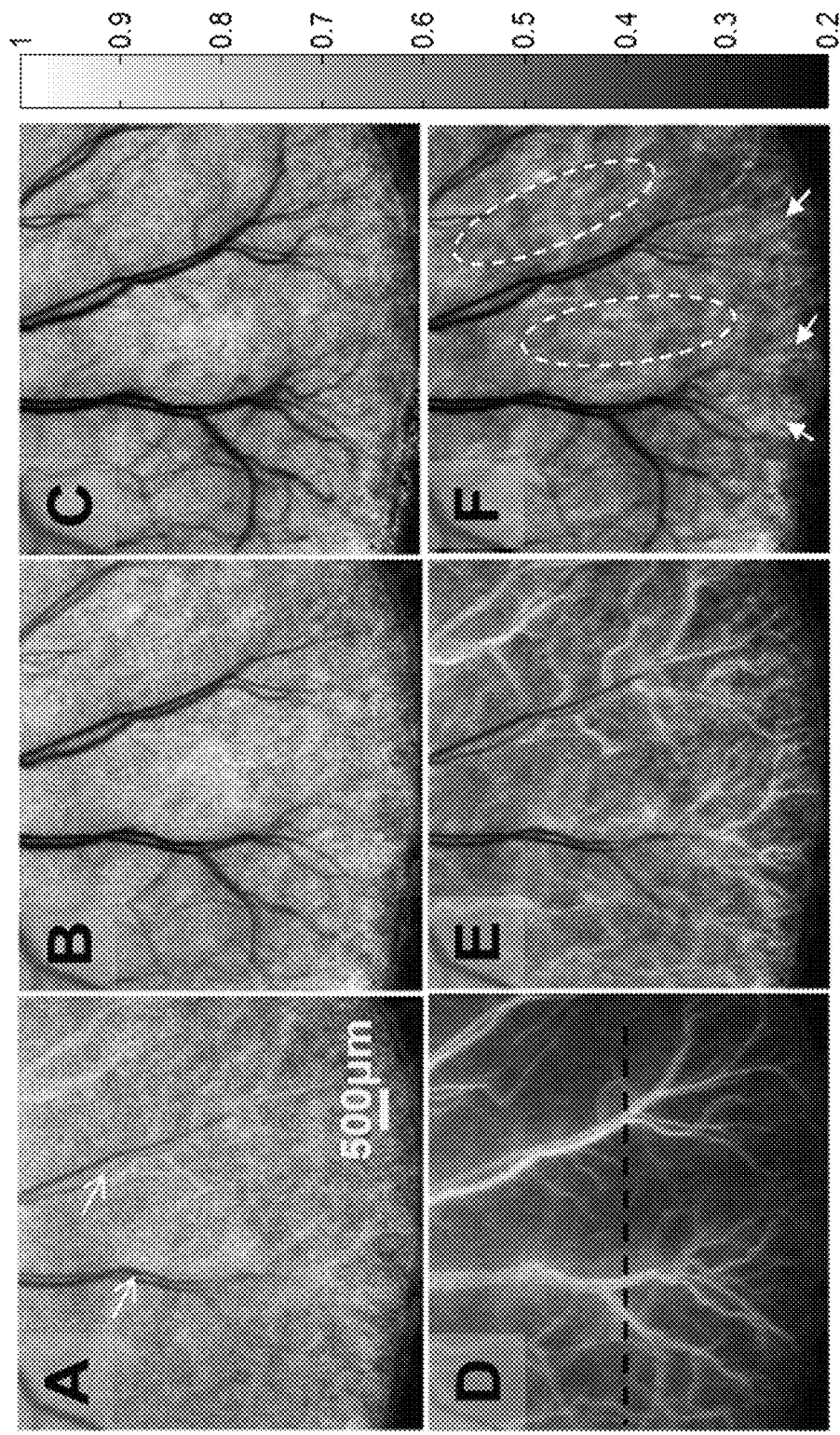
FIG. 4 shows images in the top row using LSCI imaging methods with temporal contrast $K_t$ and in the bottom row the corresponding motion enhanced contrast $\sigma_m$ images using mLSCI imaging methods for the exposure time of (A, D) 4 ms, (B, E) 10 ms and (C, F) 40 ms, respectively.

The images in the top row of FIG. 4 are the LSCI results of temporal contrast $k_t$ using the camera exposure time of FIGS. 4(A) 4 ms, 4(B) 10 ms and 4(C) 40 ms, respectively. At $\Delta t=4$ ms, it is difficult for LSCI to visualize the functional blood vessels, apart from a few large vessels (highlighted by arrows in FIG. 4(A)) that are seen with low imaging contrast. The visibility of the functioning vessels increases with the increase of the exposure time. At $\Delta t=40$ ms, the performance of LSCI imaging becomes the best. This observation is consistent with the conclusion drawn in prior LSCI studies where a long exposure time is required to image blood flow within small vessels and even to visualize lymph flows.

The images shown in the bottom row of FIG. 4 are the mLSCI results of motion enhanced contrast $\sigma_m$ under the exposure time of FIGS. 4(D) 4 ms, 4(E) 10 ms and 4(F) 40 ms, respectively. Compared to the corresponding LSCI images, the enhanced capability of mLSCI to visualize the small blood vessels (including capillaries) is clear as more blood vessels are visually delineated. First, the contrast for functional blood vessels in mLSCI, appearing 'white', is opposite to that of LSCI. Second, it is observed that the sensitivity of mLSCI to the blood flow is highly dependent upon the camera exposure time and therefore the velocity of the blood flows in the vessels. mLSCI also has an increased sensitivity to the capillary flows with an increase in camera exposure time. At $\Delta t=40$ ms, the true capillary beds (arrows and circles in FIG. 4(F)) are accessible in mLSCI, albeit with a relatively low visibility. The low visibility is due to the spatial resolution of the system which is currently at ~15 μm, while the average diameter of typical capillary vessels is between ~6-8 μm.

Theoretically, the sensitivity of LSCI to changes in blood flow depends on the exposure time and speckle correlation time. Higher sensitivity may be achieved at longer exposure time to sense the slower blood flows that give rise to an increased decorrelation time. Under the conditions of single scattering from moving particles, small scattering angles and strong tissue scattering, the correlation time is shown to be inversely proportional to the mean translational velocity of the scatters. Thus, scattering particles with slow motion correspond to longer correlation time $\tau_c$, which explains why temporal contrast may obtain the blood flow in small vessels under longer exposure time. However, a longer exposure time is equivalent to more temporal averaging, leading to blurred speckle pattern that decreases the standard deviation, which in turn reduces the imaging contrast for the fine and fast dynamic changes in the blood vessels.

However, the new motion enhanced contrast emphasizes the motion discontinuity and sparseness of scattering particles, such as RBCs. The 'whiter' the blood vessel seen in the mLSCI images, the higher the degree of the motion discontinuity in the corresponding functional vessel. The main scattering particles in the vessels are RBCs, which may be sparse when compared to the light wavelength used. When one RBC moves from one pixel to another pixel, the strength of signal recorded in the previous pixel will gradually reduce until the next RBC that comes along to fill in the pixel. This filling time interval depends on the moving velocity and the density of RBCs within the functional vessels. If the sampling rate is fast enough, this kind of motion discontinuity may be revealed by the division between two consecutive frames, giving higher imaging contrast for functional vessels, as seen in FIG. 4.

With the decrease of the sampling rate (corresponding to the increase of the camera exposure time), the "white" vessels are observed gradually shifting to the branch vessels downstream from the large ones. This phenomenon can be explained from the point of view of the moving velocity of scattering particles. The maximum speed that the motion enhanced contrast can track is when one particle travels from one pixel to another within the exposure time and its previous position is filled by another particle in the next moment. For example, if the spatial resolution of one pixel is 10 μm and the exposure time is 4 ms, the maximum moving velocity of scattering particle that may be tracked would be 2.5 mm/s under the assumption of single scattering. However, the blood flow within the capillaries (single file flow) in the mouse ear is much slower than 2.5 mm/s. Such slow motion would be frozen at the sampling rate of 250 Hz. Consequently, the 4 ms exposure time would be only sensitive to the fast blood flows in the large blood vessels as seen in FIG. 4(D). While when the camera exposure time increases to 40 ms, the maximum velocity of moving particles which may be tracked becomes 0.25 mm/s. This would be sufficient to contrast the capillary flows as shown in FIG. 4(F), where the true capillary beds, e.g. those highlighted by the arrows and circled, are visualized. However, under this circumstance, the fast flows may cause signal washout in the camera, giving the darker contrast in the resulting mLSCI image. The intermittent exposure time gives the contrast of the blood flow in functional vessels in between those delineated by $\Delta t=4$ ms and 40 ms (see, e.g., FIG. 4(E)).

Figure 5:
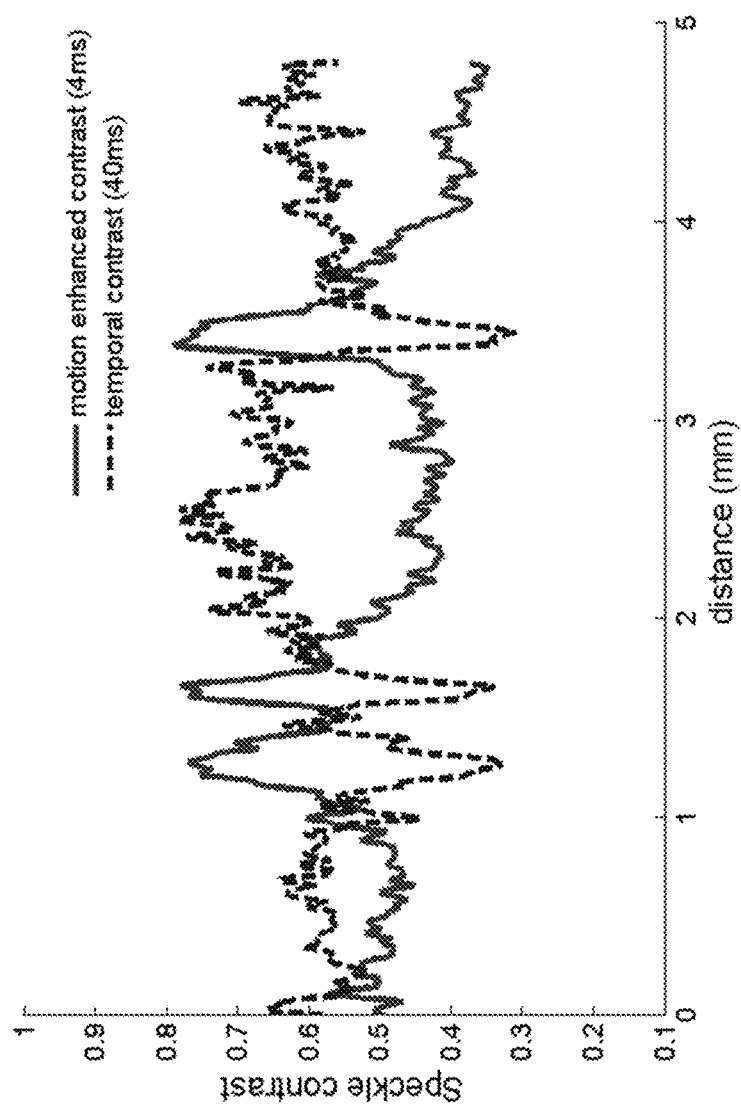
FIG. 5 shows a graph comparing the motion enhanced contrast (at an exposure time of 4 ms) with the temporal contrast (at an exposure time of 40 ms) along the horizontal dashed line shown in FIG. 4(D).

To compare further LSCI and mLSCI, one horizontal line was chosen (the black line in FIG. 4(D)) to plot the resulting contrast curves in FIG. 5, where the comparison was made between the motion contrast under the exposure time of 4 ms and the temporal contrast under the exposure time of 40 ms. Notably, the peaks in $\sigma_m$ (mLSCI) exactly correspond to the valley of $K_t$ (LSCI), and the mLSCI and LSCI curves are opposite to each other, indicating the motion enhanced contrast suppresses maximally the static scattering effect thanks to a subtraction operation between adjacent division frames. Although opposite, the similarity between the two curves implies that the sensitivity of the motion contrast under $\Delta t=4$ ms is comparable to that of temporal contrast under $\Delta t=40$ ms, demonstrating the dramatically improved capability of mLSCI to image the functional blood flows within microcirculatory tissue beds in vivo. The repeatability of this observation and thus the conclusion was validated on a number of mice in vivo in the experiments (n>5).

In summary, a speckle motion enhanced contrast analysis method may be used to visualize dynamic blood flows, including capillary beds, in vivo, where the division and subtraction are applied to adjacent frames from a series of successive frames in order to enhance the motion contrast of scattering particles. The sensitivity of the proposed method to the blood flow is highly dependent upon the exposure time of the digital camera used to record the dynamic speckle patterns emerging from the living tissue.

EXAMPLE 2

Working Example for Optical Coherence Tomography Based Microangiography

As discussed above, optical coherence tomography ("OCT") is a non-invasive method for providing high resolution (~10 μm) and three-dimensional images of microstructures within biological tissues. Optical microangiography ("OMAG") is a technique for processing an OCT dataset that allows the extraction of the three-dimensional microvasculature from the OCT images, with capillary resolution. An example of OCT and OMAG utilizing the present methods is described below.

System Setup

Figure 6:
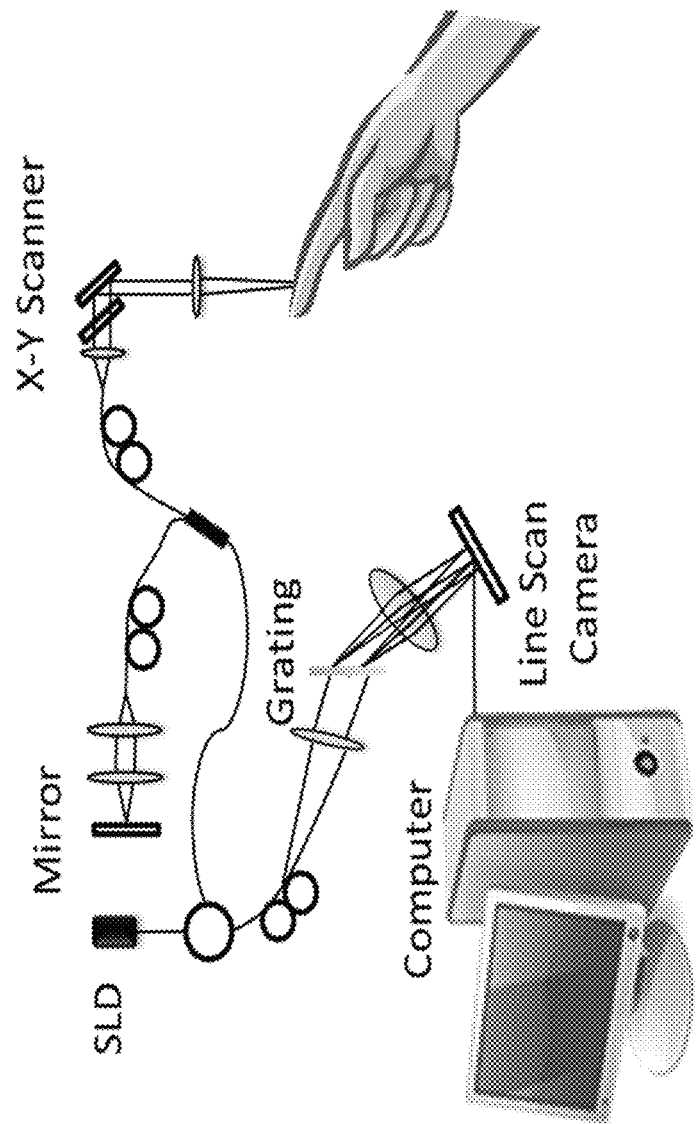
FIG. 6 shows a schematic of a Fourier domain optical coherence tomography system, according to one embodiment, in which an index finger is the target tissue.

A home-built Fourier domain OCT system was used to image an in vivo sample, as presented in FIG. 6. The light for the OCT system was provided by a superluminescent diode ("SLD"). The light source had a central wavelength of 1340 nm and a full width half maximum ("FWHM") of 110 nm which provides an axial resolution of ~7 μm in air. The light is divided into two arms. One arm is transmitted to the biological tissue, while the other arm is transmitted to a reference mirror. In the sample arm, the light was directed to a collimating lens, an XY galvanometer and an objective lens. The XY galvanometer enabled the collection of a 3D dataset of the sample, in which X-scanner (fast scan) provides a cross-sectional (x-z) image, i.e. B-scan (B-frame), and Y-scanner (slow scan) when working together with X-scan gives 3D imaging of the sample, i.e. C-scan. The objective lens has a 10× magnification and an 18 mm focal length, which provides a lateral resolution of ~7 μm. The light that was reflected from the reference mirror and the biological tissues was combined to produce an interference signal which was detected by a spectrometer and analyzed with a computer. The analysis of the interference spectrum captured by the spectrometer provided a depth-scan (z direction), also known as A-scan. The spectrometer had a spectral resolution of ~0.141 nm and provided an imaging depth of ~3 mm (~2.0 mm in tissue) at each side of the zero delay line. The spectrometer used an InGaAs camera (Goodrich Inc.) with an A-scan rate of 92 k Hz. The system had a measured dynamic range of 105 dB with the light power of 3.5 mW at the sample surface. By collecting 400 A-lines per B-frame, a frame rate of 180 fps was obtained.

Optical Microangiography

As discussed above, OMAG is a method for processing OCT data that enables the extraction of blood vessels in three-dimensional space with high resolution, and without using contrast agents. The movement of cells within the blood vessels acts as the contrast for OMAG imaging. The OMAG method may be applied in either the fast (x-scan) or slow axis (y-scan). When OMAG is used in the fast axis, it is sensitive to the fast blood flow rate which is commonly found in the large vessels. On the other hand, when OMAG is applied on the slow axis, it is sensitive to the fast and slow blood flow rate. In this study, we applied OMAG in the slow axis to increase the sensitivity of the small vessels such as the capillaries.

The data collected by an OCT camera can be expressed as:

$$I(t,k) = 2S(k)E_R \left[ \int_{-\infty}^{\infty} a(z,t)\cos[2kn(t)z]\,dz + a(z_1)\cos[2kn(t)(z_1 - vt)] \right] \quad (1)$$

where k is the wavenumber ($2\pi/\lambda$), $\lambda$ is the wavelength of the light, t is the time point when the data is captured, $E_R$ is the light reflected from the reference mirror, S(k) is the spectral density of the light source, n is the tissues index of refraction, z is the depth position, a(z,t) is the amplitude of the back scattered light, v is the velocity of the moving blood cells located at depth $z_1$. The self-cross-correlation between the light backscattered within the sample was not considered given its weak signal.

The depth information (I(t,z)) is obtained by calculating the Fourier transform ("FT") of the spectrum. The result provides a complex term that contains a magnitude (M(t,z)) and a phase ($\phi$(t,z)), given by:

$$I(t,z) = FT[I(t,k)] = M(t,z)e^{i\phi(t,z)} \quad (2)$$

An OCT B-frame image (I(x,z)) can be provided by taking the magnitude of the above equation, where t is replaced with the variable x. Traditional OMAG uses high pass filtering to isolate the high frequency signal (moving particles) from the low frequency signal (static tissue). This is typically done by taking a differential operation across the slow-axis:

$$I_{flow}(x_i, z) = \frac{\sum_{i=1}^{N} |I(x_{i+1}, z) - I(x_i, z)|}{N} \quad (3)$$

where i represents the index of the B-scan and N is the total number of frames that are averaged together.

The Proposed Method.

In the proposed method, in order to enhance the moving contrast from the flowing RBC cells, division operation is performed between the adjacent B-scans, $$D(x_i, z) = I(x_{i+1}, z)/I(x_i, z) \quad (4)$$

And then the blood flow image is obtained by using high pass filtering to isolate the high frequency signal (moving particles) from the low frequency signal (static tissue). This can be done using three methods:
1) applying Equation (3),
2) taking the standard deviation of Equation (4), and
3) applying Fourier transformation of Equation (4) against $x_i$ (or t) and then using a high pass filtering to isolate high frequency signals.

Demonstration

In this demonstration, we used the OCT system described above to obtain microvasculature within a mouse skin tissue in vivo. The scanning protocol was based on the ultrahigh sensitive OMAG method. The x-scanner (fast) was controlled by using a saw tooth function, while the y-scanner (slow) was controlled by a step function. Both scanners imaged a range of 2.5×2.5 mm² through the sample. Each B-scan contained 400 A-lines, there were 400 positions in the slow-direction (C-scan), and at each position 5 B-frames were acquired. The whole 3D image was acquired within ~11 seconds.

Figure 7:
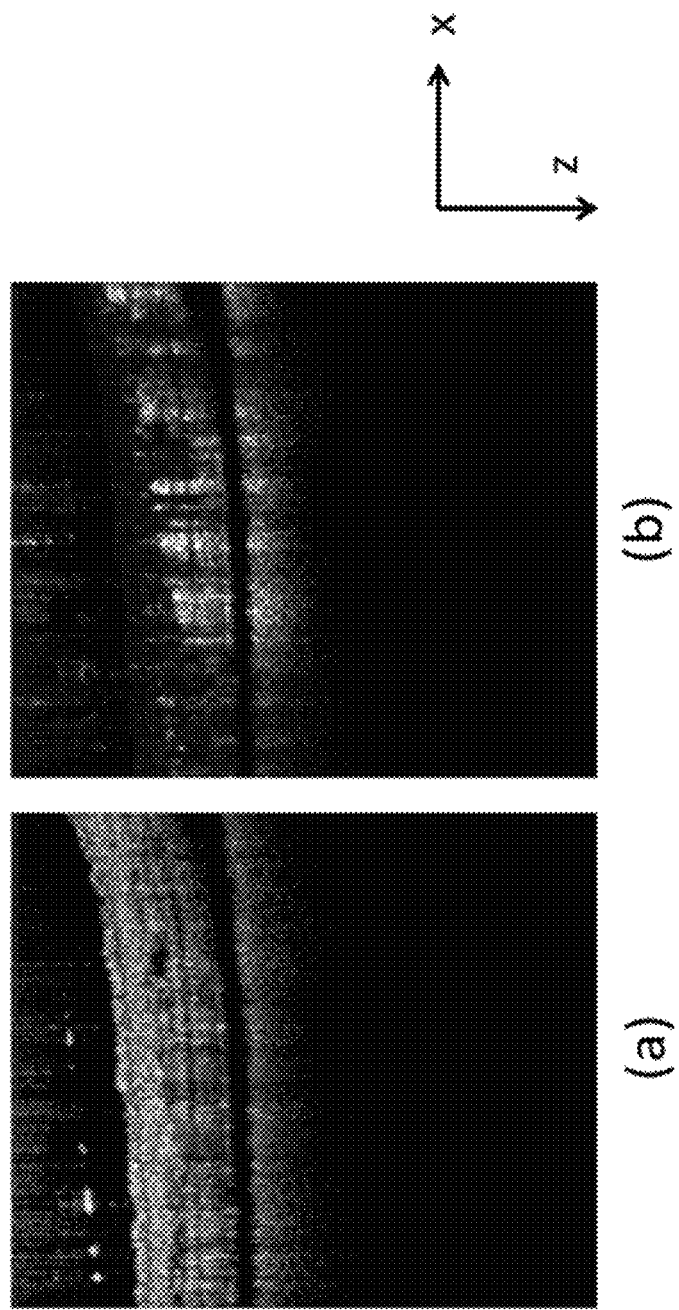
FIG. 7 shows the results of a B-scan from Example 2 below, where (a) is the typical Optical Coherence Tomography ("OCT") structural image (B-frame), and (b) is the corresponding blood flow image.

By the use of the differential operation of Equation (4) and then averaging, i.e. (Eq. 3), FIG. 7 shows the results of a B-scan, where (a) is the typical OCT structural image (B-frame), and (b) is the corresponding blood flow image, where it can be seen that blood flow is contrasted very well. Note that the size of the image is x-z=2.5×2.0 mm² in tissue.

Figure 8:
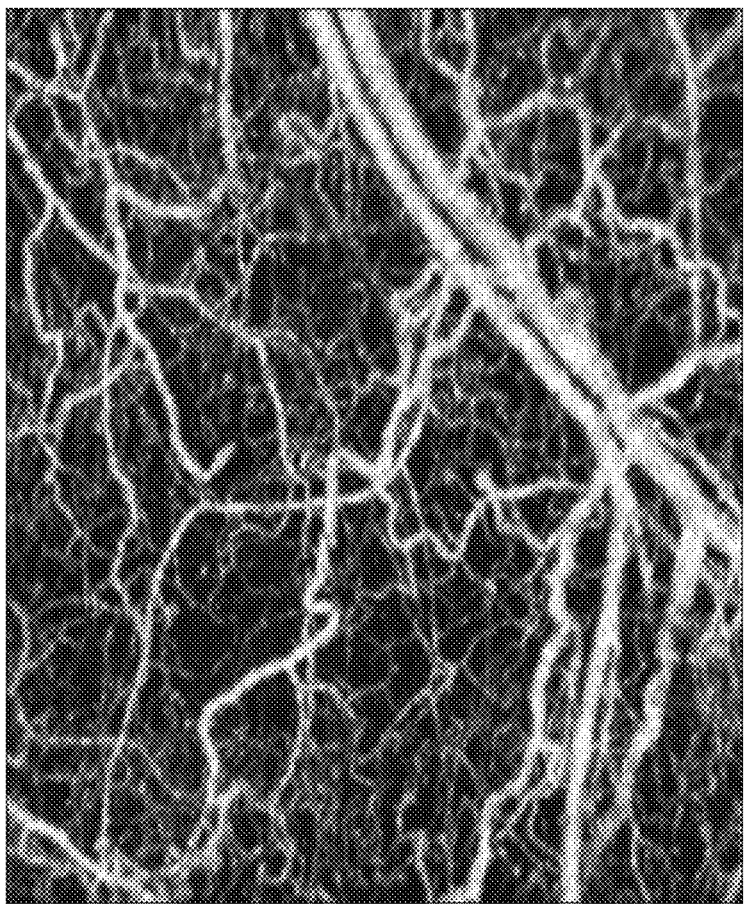
FIG. 8 shows a 3-D OCT image of microvasculature innervating a tissue bed presented in an x-y projection image, such that the z-direction is collapsed.

The result presented in FIG. 7 is only one frame. If a 3-D dataset is collected, then a 3-D image of microvasculature innervating the tissue bed may be obtained. FIG. 8 shows such an example (presented in x-y projection image, i.e. z direction is collapsed), where it can be seen that both the big vessels and small capillary vessels are clearly visualized by the use of proposed method. The size of the image in FIG. 8 is x-y=2.5× 2.5 mm².

The invention claimed is:
1. A method, the method comprising:
directing a light beam at a blood-perfused target tissue;
reflecting the directed light beam off of static target tissue and flowing cells;
capturing a plurality of digital images of interference patterns of the reflected light in a plurality of successive frames;

measuring, via a processor, a light intensity of at least one pixel of each digital image, wherein the at least one pixel corresponds to an identical pair of coordinates in each successive frame;

comparing the measured light intensity of the at least one pixel of each digital image to the measured light intensity of the at least one pixel of an adjacent frame at the identical pair of coordinates thereby enhancing a light saturation profile for the at least one pixel of each frame; and determining, via the processor, a compiled light intensity for the at least one pixel for an aggregate motion contrast image based upon the enhanced light saturation profile of the at least one pixel for each frame.

2. The method of claim 1, wherein the plurality of successive frames are captured at a sampling frequency ranging from 1 Hz to 1,000,000 Hz.

3. The method of claim 1, wherein a camera exposure time per frame ranges from about 1 micro-second to about 1 second.

4. The method of claim 1, wherein each of the plurality of digital images is a laser-speckle image produced by scattering of the light beam off of the target tissue and flowing cells.

5. The method of claim 1, wherein each of the plurality of digital images is an optical coherence tomography cross-section image produced by an optical coherence tomography imaging system when the light beam is scattered off of the target tissue and flowing cells.

6. The method of claim 1, wherein comparing the measured light intensity of the at least one pixel of each digital image to the measured light intensity of the at least one pixel of the adjacent frame at the identical pair of coordinates thereby enhancing the light saturation profile for the at least one pixel of each frame comprises differentiating or dividing the value of the measured light intensity for the at least one pixel of each digital image by the value of the measured light intensity for the at least one pixel of the adjacent frame at the identical pair of coordinates thereby obtaining a light intensity difference or a light intensity quotient for the at least one pixel of each frame.

7. The method of claim 6, wherein determining, via the processor, the compiled light intensity for the at least one pixel for the aggregate motion contrast image based upon the enhanced light saturation profile of the at least one pixel for each frame comprises determining for each pixel of the motion contrast image a mean of the light intensity differences, a mean of the light intensity quotients or a mean of differences between the light intensity quotient for the at least one pixel of each digital image and a light intensity quotient for the at least one pixel of the adjacent frame at the identical pair of coordinates.

8. The method of claim 6, wherein determining, via the processor, the compiled light intensity for the at least one pixel for the aggregate motion contrast image based upon the enhanced light saturation profile of the at least one pixel for each frame comprises determining for the at least one pixel of the aggregate motion contrast image a sample standard deviation of the light intensity differences or a sample standard deviation of the light intensity quotients for the at least one pixel of each frame or a sample standard deviation of a difference between the light intensity quotient for the at least one pixel of each digital image and a light intensity quotient for the at least one pixel of the adjacent frame at the identical pair of coordinates.

9. The method of claim 6, wherein comparing the measured light intensity of the at least one pixel of each digital image to the measured light intensity of the at least one pixel of the adjacent frame at the identical pair of coordinates thereby enhancing a light saturation profile for the at least one pixel of each frame further comprises:

performing Fourier transformation of the light intensity differences or of the light intensity quotients for the at least one pixel of each frame or Fourier transformation of a difference between the light intensity quotient for the at least one pixel of each digital image and a light intensity quotient for the at least one pixel of the adjacent frame at the identical pair of coordinates; and transforming a signal associated with the at least one pixel of the aggregate motion contrast image.

10. The method of claim 9, wherein determining, via the processor, the compiled light intensity for the at least one pixel for the aggregate motion contrast image based upon the enhanced light saturation profile of the at least one pixel for each frame further comprises performing high-pass filtering of a Fourier-transformed signal for the at least one pixel of the aggregate motion contrast image.

11. The method of claim 1, wherein the method is used to monitor blood flow within living tissue.

12. The method of claim 1, wherein the at least one pixel of each digital image of each frame comprises a plurality of pixels.

13. A method, the method comprising:

directing a light beam at a blood-perfused target tissue;

reflecting the directed light beam off of static target tissue and flowing cells;

capturing a plurality of digital images of interference patterns of the reflected light in a plurality of successive frames (N);

measuring, via a processor, a light intensity of at least one pixel of each digital image, wherein the at least one pixel corresponds to an identical pair of coordinates (x, y) in each successive frame, wherein $I_i(x,y)$ is the light intensity of the at least one pixel (x, y) in a frame i, wherein the frame i corresponds to i=1, 2, ... N;

comparing the measured light intensity of the at least one pixel (x, y) of each digital image to the measured light intensity of the at least one pixel (x, y) of an adjacent frame at the identical pair of coordinates (x, y) thereby enhancing a light saturation profile for the at least one pixel of each frame; and determining, via the processor, a compiled light intensity for the at least one pixel (x, y) for an aggregate motion contrast image based upon the enhanced light saturation profile of the at least one pixel (x, y) for each frame.

14. The method of claim 13, wherein comparing the measured light intensity of the at least one pixel of each digital image to the measured light intensity of the at least one pixel of the adjacent frame at the identical pair of coordinates thereby enhancing the light saturation profile for the at least one pixel of each frame comprises determining a light intensity difference for the at least one pixel of each frame based upon $D_i(x, y)=I_i(x, y)-I_{i+1}(x, y)$ or determining a light intensity quotient for the at least one pixel of each frame based upon $D_i(x, y)=I_i(x, y)/I_{i+1}(x, y)$.

15. The method of claim 14, wherein determining, via the processor, a compiled light intensity for the at least one pixel (x, y) for an aggregate motion contrast image based upon the enhanced light saturation profile of the at least one pixel (x, y) for each frame comprises determining for the at least one pixel (x, y) of the aggregate motion contrast image a mean of the light intensity differences or a mean of the light intensity quotients based upon $$\overline{D}(x, y) = \frac{1}{N}\sum_{i=1}^{N} D_i(x, y)$$

or a mean of differences in the light intensity quotients based upon $$\overline{\Delta D}(x, y) = \frac{1}{N}\sum_{i=1}^{N} \Delta D_i(x, y).$$

16. The method of claim 14, wherein determining, via the processor, a compiled light intensity for the at least one pixel (x, y) for an aggregate motion contrast image based upon the enhanced light saturation profile of the at least one pixel (x, y) for each frame comprises determining for the at least one pixel of the aggregate motion contrast image a sample standard deviation of the light intensity differences or a sample standard deviation of the light intensity quotients of the at least one pixel (x, y) of each frame based upon $$\sigma_m(x, y) = \sqrt{\sum_{i=1}^{N} [D_i(x, y) - \overline{D}(x, y)]^2 / (N-1)}$$

or a standard deviation of the differences in light intensity quotients of the at least one pixel (x, y) of each frame based upon $$\sigma_m(x, y) = \sqrt{\sum_{i=1}^{N} [\Delta D_i(x, y) - \overline{\Delta D}(x, y)]^2 / (N-1)}.$$

17. The method of claim 14, wherein comparing the measured light intensity of the at least one pixel (x, y) of each digital image to the measured light intensity of the at least one pixel (x, y) of the adjacent frame at the identical pair of coordinates (x, y) thereby enhancing the light saturation profile for the at least one pixel (x, y) of each frame further comprises:
performing Fourier transformation of the light intensity differences or of the light intensity quotients, $D_i(x, y)$, for the at least one pixel of each frame or Fourier transformation of differences in light intensity quotients, $\Delta D_i(x, y)$, for the at least one pixel of each frame and transforming a signal associated with the at least one pixel of the aggregate motion contrast image; and
transforming a signal associated with the at least one pixel of the aggregate motion contrast image.

18. The method of claim 17, wherein determining, via the processor, a compiled light intensity for the at least one pixel (x, y) for an aggregate motion contrast image based upon the enhanced light saturation profile of the at least one pixel (x, y) for each frame comprises performing high-pass filtering of the Fourier-transformed signal for the at least one pixel of the aggregate motion contrast image.

19. The method of claim 13, wherein the at least one pixel of each digital image of each frame comprises a plurality of pixels.

* * * * *